US00PP08159P

United States Patent [19]

Dehan

[11] Patent Number: Plant 8,159

[45] Date of Patent: Feb. 23, 1993

[54] ASTER PLANT NAMED SUNTOP

[75] Inventor: Klara Dehan, Holon, Israel

[73] Assignee: Danziger - "Dan" Flower Farm, Post Beit Dagan, Israel

[21] Appl. No.: 687,162

[22] Filed: Apr. 19, 1991

[51] Int. Cl.[5] ..... A01H 5/00

[52] U.S. Cl. ..... Plt./68.1

[58] Field of Search ..... Plt./68, 68.1

*Primary Examiner*—James R. Feyrer

*Attorney, Agent, or Firm*—Foley & Lardner

[57] ABSTRACT

An aster plant named Suntop characterized by its blue-violet flower color, double flower form, extensive secondary branching, and floriferous habit, with flowering being concentrated near the tops of the branches.

1 Drawing Sheet

The present invention comprises a new and distinct cultivar of aster hybrid, hereinafter referred to by the cultivar name Suntop.

The new cultivar was originated from a cross made by applicant in a controlled breeding program in Mishmar Hashiva, Israel. The female, or seed, parent was a cultivar designated 34DP-1. The male, or pollen, parent was a cultivar designated 2-DD-4. Both parents are hybrids of aster cultivars, species unknown.

Suntop was discovered and selected by applicant as a flowering plant within the progeny of the stated cross in a controlled environment in Mishmar Hashiva, Israel. Asexual reproduction of the new cultivar by vegetative cuttings, as performed by applicant at Mishmar Hashiva, Israel, has demonstrated that the combination of characteristics as herein disclosed for the new cultivar are firmly fixed and retained through successive generations of asexual reproduction.

Suntop has not been observed under all possible environmental conditions. The phenotype may vary significantly with variations in environment such as temperature, light intensity and day length, without, however, any variance in genotype. The following observations, measurements and comparisons describe plants grown in Mishmar Hashiva, Israel under conditions which closely approximate those generally used in commercial practice.

The following traits have been repeatedly observed and are determined to be basic characteristics of Suntop which, in combination, distinguish this aster as a new and distinct cultivar:

1. The petal color of the flower is unique to the species, comprising an intense, relatively dark violet.
2. The shape of the flower is unique, being comprised of two rows of petals.
3. Secondary branching is extensive, producing a highly spreading plant shape.
4. Suntop is very floriferous, with flowering occuring on all of its many secondary branches. Moreover, the flowers per stem ratio is high, so that the total number of flowers produced is much higher than other varieties of the species with which applicant is familiar.
5. Flowering is concentrated near the tops of the branches, thereby producing profuse flowering at the periphery of the plant, as well as below.

The unique characteristics of the new cultivar makes it difficult to provide a meaningful comparison with other cultivars of the species. The female parent can be generally described as having dark pink ray floret color, long stems and early flowering. The male parent is characterized by its very dark pink petal color which tends towards purple.

The accompanying color photographic drawings show a typical specimen plant of the new cultivar.

The top photograph shows in perspective view a section of the plant with the bottom photo comprising a closeup view of a single flower.

The petal color illustrated in the photographs is significantly lighter than the true color, which is set forth below.

In the following description, color references are made to The Royal Horticultural Society Color Chart (RHS), except where general colors of ordinary significance are referred to. Color values were taken at approximately noon on Jan. 20, 1991 under artificial light at Mishmar Hashiva, Israel.

Botanical classification: Aster hybrid cv Suntop.

Parentage:

*Male parent.*—2-DD-4.

*Female parent.*—34DP-1.

Propagation: By stem cuttings, tissue culture and division.

INFLORESCENCE

A. Capitulum:

*Form.*—Daisy, flat.

*Type.*—Double, with about 43 total petals appearing in two rows.

*Diameter across face.*—2-2.5 cm.

B. Flowering season: Natural flowering in Israel is around September 15. In photoperiodic programs, the flower response is approximately six weeks of short days following four weeks of long days for elongation.

C. Quantity: Due to its extensive secondary branching and high ratio of flowers per stem, total flower production is unusually high.

D. Corolla of ray florets:

*Color (general tonality from a distance of three meters).*—Violet-blue.

*Color (upper surface).*—83C.

*Color (under surface).*—90D.

E. Corolla of disc florets:

*Color (mature).*—Light yellow 2C.

*Color (immature).*—Light yellow 5A.

*Diameter of disc.*—0.75-1.0 cm.

F. Reproductive organs:

*Androecium.*—Light yellow, 1A.

*Gynoecium.*—Light yellow to light green, 1C.

PLANT

A. General Appearance: Generally tall and very spreading. After completion of short day treatment as described for flowering, main stem is 1–1.2 meters tall.

B. Foliage:

*Color.*—137B.

*Shape.*—Typically elongated, with typical leaf being 10–11 cm. long and 1.5 cm wide.

I claim:

1. A new and distinct cultivar of aster plant named Suntop, as illustrated and described.

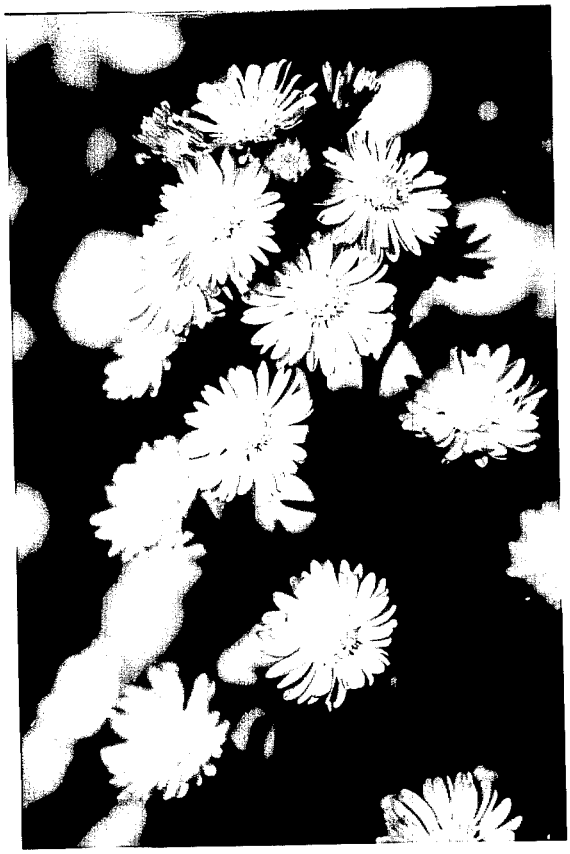
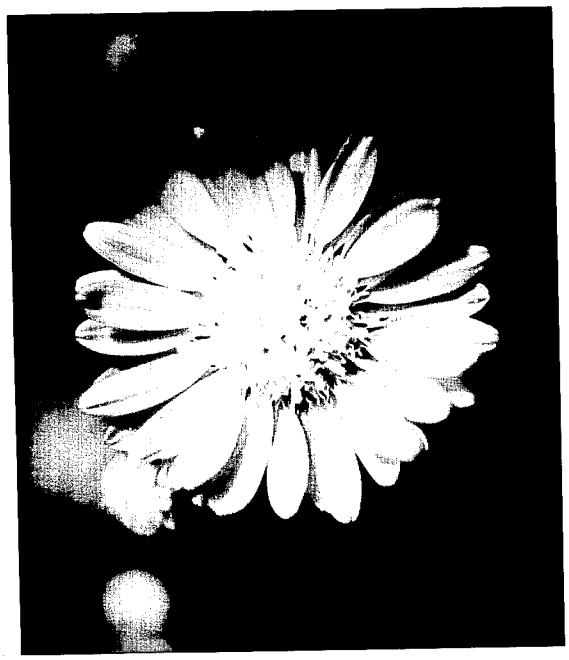

* * * * *